United States Patent [19]

Wang

[11] Patent Number: 4,953,189
[45] Date of Patent: Aug. 28, 1990

[54] X-RAY RADIOGRAPHY METHOD AND SYSTEM

[75] Inventor: Shih-Ping Wang, Los Altos, Calif.
[73] Assignee: Hologic, Inc., Waltham, Mass.
[21] Appl. No.: 256,846
[22] Filed: Oct. 12, 1988

Related U.S. Application Data

[63] Continuation of Ser. No. 797,837, Nov. 14, 1985.

[51] Int. Cl.⁵ .............................................. H05G 1/44
[52] U.S. Cl. ..................................... 378/108; 378/146
[58] Field of Search ............ 378/16, 65, 108, 145–157, 378/66, 113

[56] References Cited

U.S. PATENT DOCUMENTS

| 4,366,576 | 12/1982 | Annis . | |
|---|---|---|---|
| 4,433,430 | 2/1984 | Fredzell | 378/108 |
| 4,675,893 | 6/1987 | Duinker et al. | 378/151 |
| 4,677,652 | 6/1987 | Duinker et al. | 378/151 |
| 4,715,056 | 12/1987 | Vlasbloem et al. | 378/146 |
| 4,741,012 | 4/1988 | Duninker et al. | 378/145 |
| 4,773,087 | 9/1988 | Plewes | 378/146 |
| 4,785,471 | 11/1988 | Boersma | 378/146 |
| 4,803,714 | 2/1989 | Vlasbloem | 378/62 |
| 4,890,312 | 12/1989 | Duinker | 378/146 |

FOREIGN PATENT DOCUMENTS 0158382 10/1985 European Pat. Off. .
0220770  5/1987 European Pat. Off. .
2485790  6/1980 France .
WO84/04878 12/1984 PCT Int'l Appl. .

OTHER PUBLICATIONS

Vlasbloem, H. et al., Amber: A Scanning Multiple-Beam Equalization System for Chest Radiography, Radiology, vol. 169, No. 1, Oct. 1988, pp. 29–34.

Primary Examiner—Constantine Hannaher
Assistant Examiner—David P. Porta
Attorney, Agent, or Firm—Cooper & Dunham

[57] ABSTRACT

A method and device for producing flux equalized x-ray images for medical radiography through the use of a scanning fan shaped x-ray beam and a feedback control system which regulates the beam intensity at a multiple number of points along the fan beam to compensate for the x-ray attenuation variations of the patient.

52 Claims, 5 Drawing Sheets

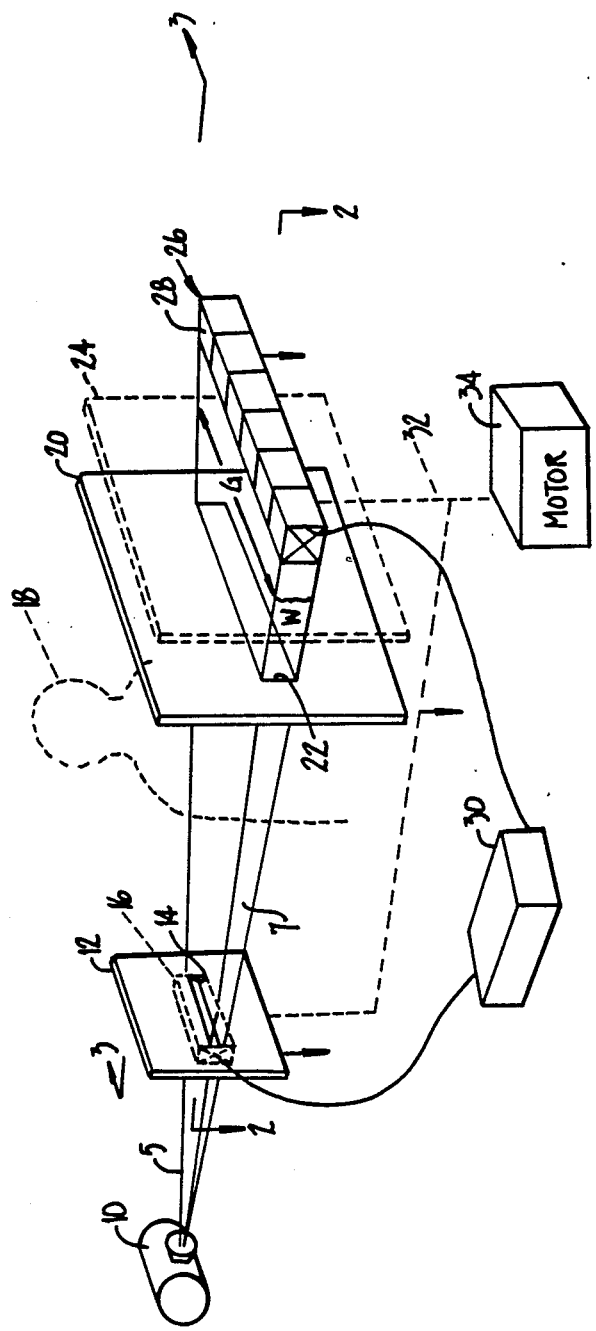
FIG._1.

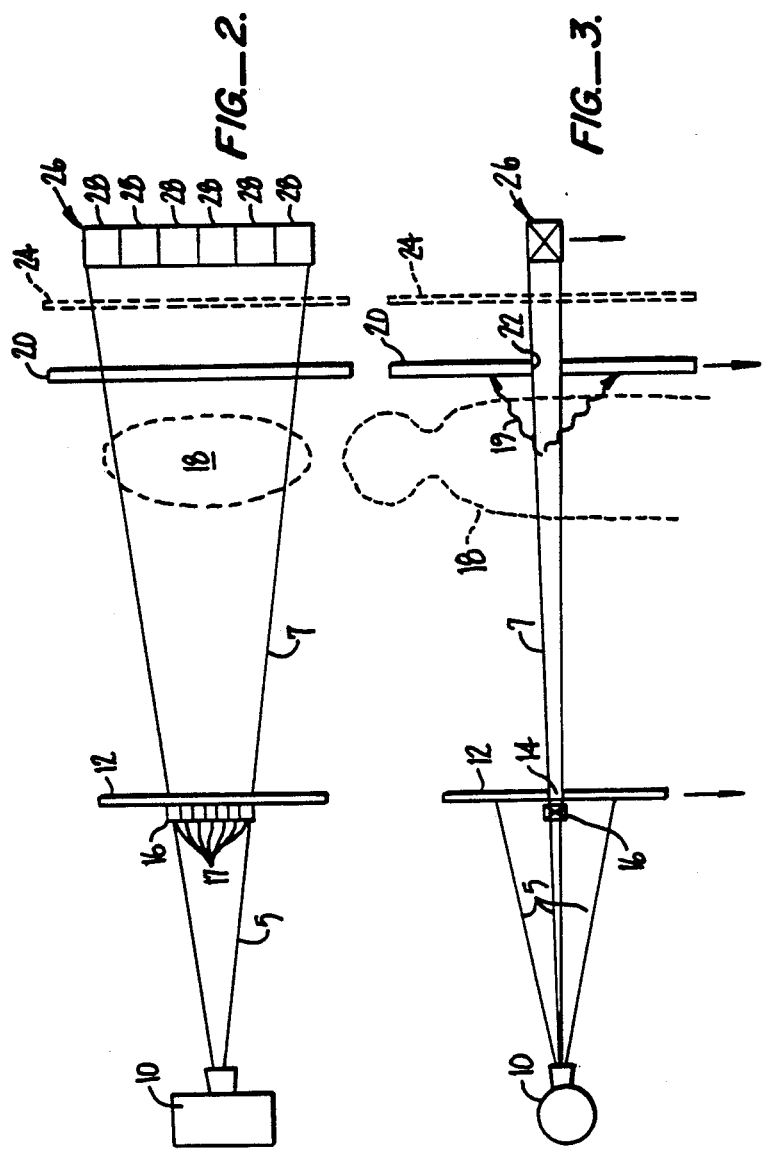

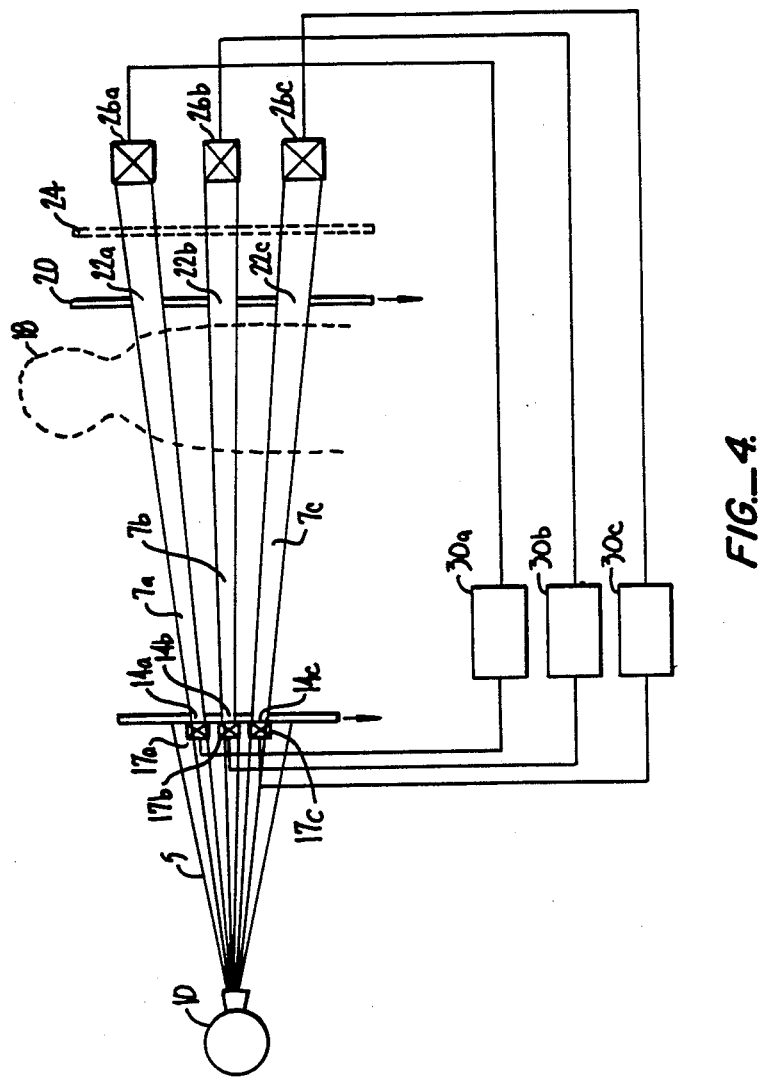
FIG._4.

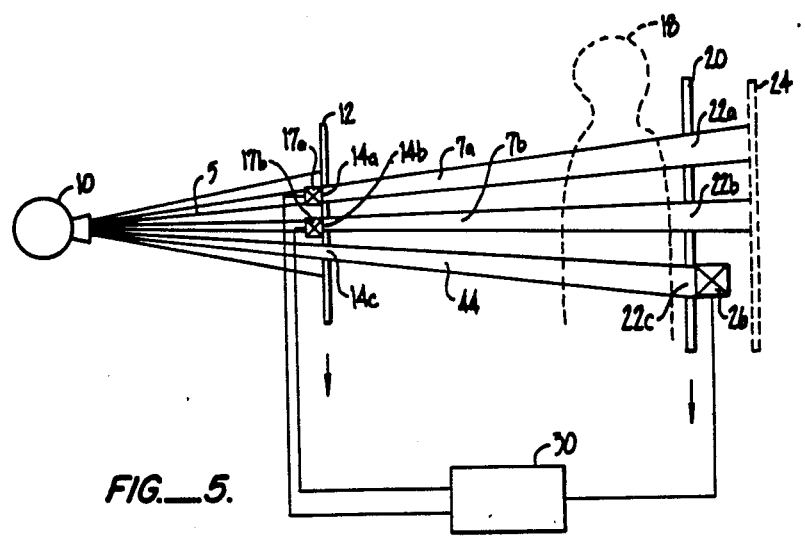
FIG._5.
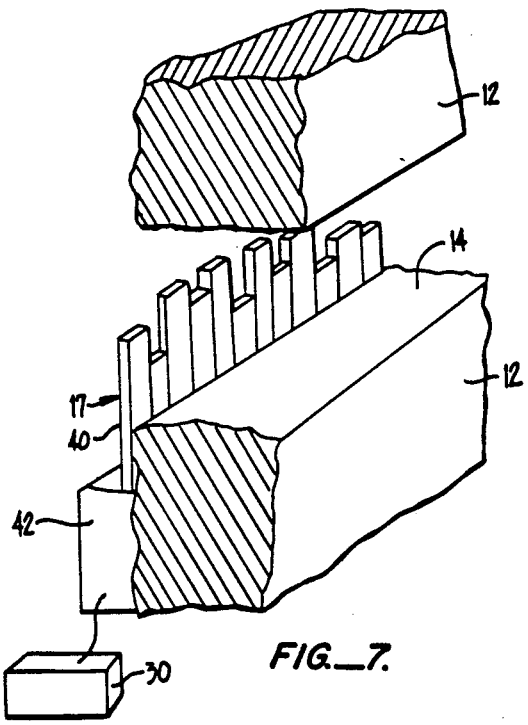
FIG._7.

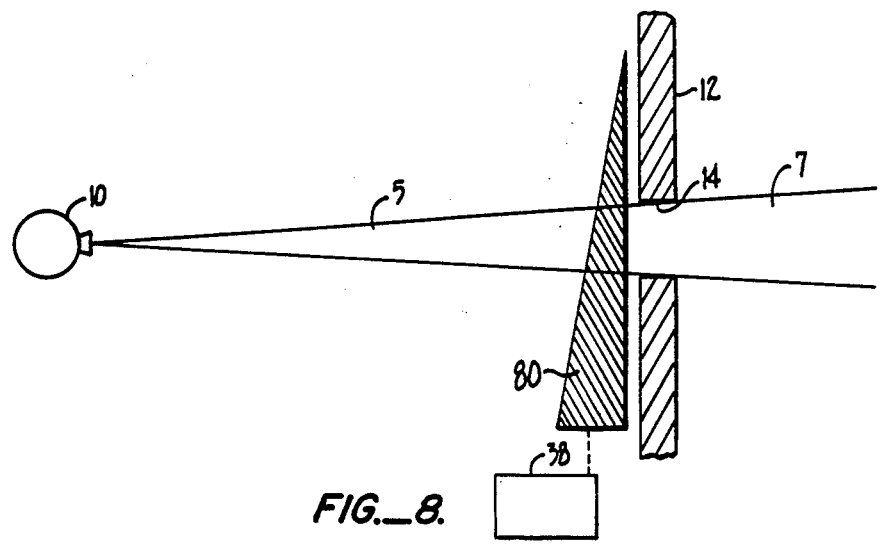
FIG._8.
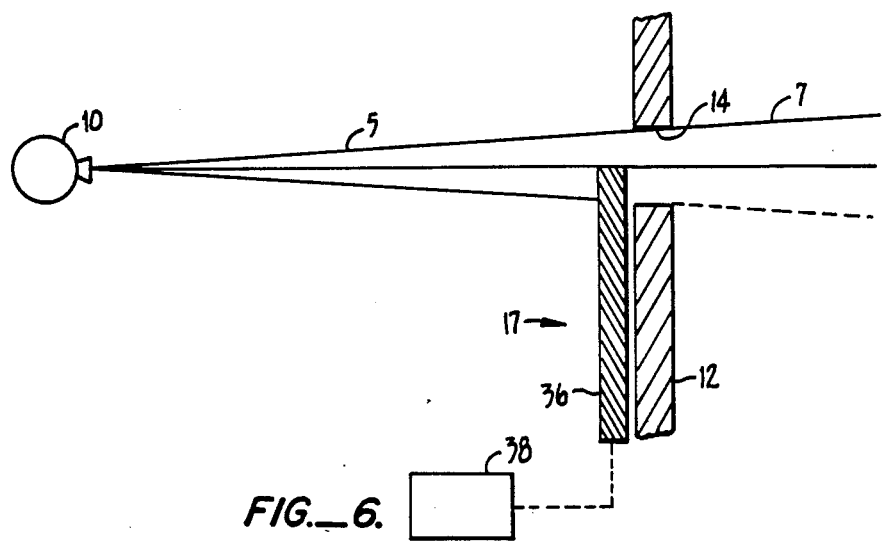
FIG._6.

X-RAY RADIOGRAPHY METHOD AND SYSTEM

This is a continuation of Application Ser. No. 797,837, filed Nov. 4, 1985.

DESCRIPTION

1. Technical Field

This invention relates to a device and method of producing feedback controlled flux equalized x-ray images with the principal application being in medical radiography.

2. Background Art

Frequently, the dynamic response range of an x-ray imaging system is less than the x-ray attenuation range of the object to be imaged This situation is encountered often by the conventional x-ray radiography system, which is comprised of a film-screen cassette as the detector-recorder for x-ray images and an x-ray source with a broad and spatially uniform beam. This system has been in popular use since the discovery of x-rays about ninety years ago. The medical x-ray film typically has a very high contrast enhancement factor, which is often called the contrast gradient or gamma, resulting in a very narrow latitude (or exposure range). This high contrast enhancement factor is a necessary feature of an x-ray film because typical anatomical objects to be detected have very low x-ray contrast so that their image on the x-ray film would be too faint for the physicians to see if the contrast enhancement factor were lowered.

In most x-ray examinations, such as a chest examination, the typical patient exhibits very large anatomical thickness variations and, thus, very large x-ray attenuation variations That is, some anatomical parts are very opaque to x-rays and some other parts are very transparent to x-rays. As a result, x-ray films of these examinations, due to the narrow exposure range of the x-ray film, are optimally exposed for only a portion of the entire picture, leaving large portions of the picture either overexposed or underexposed. The contrast enhancement factor for both the overexposed and the underexposed regions is much lower than that of the optimally exposed regions. Therefore, there is significant loss of x-ray information (and loss of diagnostic value) in the overexposed and underexposed regions of the x-ray film.

For example, in a typical PA chest film, the lung field is usually optimally exposed by choice, and the mediastinal and subdiaphragmatic areas are left underexposed. The probability of detecting tumors and other abnormalities located in the underexposed areas is significantly lower than the detection probability in the lung field, where the exposure is optimum. This non-uniform exposure of the x-ray film, which is due primarily to the large thickness variations in a typical patient, is a major shortcoming in conventional x-ray radiography systems. The image quality and diagnostic value of the x-ray film can be improved significantly if the non-uniform exposure effect caused by these thickness variations in the patient can be reduced.

Indeed, Pennington et al (Proc. SPIE, volume 233, pages 176–182 (1980)), Plewes et al ((A) Radiology, volume 142, pages 765–768 (1982); and (b) Diagnostic Imaging, October 1985, pages 85–96), and others have demonstrated that nodule detection in chest films can be significantly improved with some compensating means by which the non-uniformity in the exposure is reduced. These compensating means all involve spatial modulation of the x-ray flux so that the flux at the x-ray film is more or less equalized. The process is frequently called the flux equalization method.

In order to provide flux equalization to all varieties of patients, feedback controls have to be added to the flux equalization processes. That is, flux equalization is provided after some spatial attenuation information has been obtained on the specific patient who is being examined. It is important to point out here that in carrying out the feedback controlled flux equalization process, one must not generate new problems such as patient motion unsharpness resulting from prolonged exposure time, artifacts from compensation misregistration, increased patient dosage, excessive heat loading on the x-ray tube target, increasing the effect of scattered x-rays, and user or patient inconveniences.

There exists a large body of feedback controlled flux equalization prior art. Representative of the prior art using a x-ray mask are U.S. Pat. Nos. 3,755,672 (Edholm et al) and U.S. Pat. No. 4,497,062 (Mistretta et al). Representative of the prior art using an optical mask is U.S. Pat. No. 4,322,619 (Nelson et al). Prior art using a raster scanned x-ray target to generate a scanning pencil beam of x-rays is represented by U.S. Pat. No. 2,837,657 (Craig et al). Prior art using a mechanically moved scanning aperture to generate a scanning pencil beam of x-rays is represented by Plewes et al (Medical Physics, volume 10, pages 655–663 (1983)). Prior art using a scanning fan beam are represented by U.S. Pat. No. 4,433,430 (Fredzell) and Plewes et al (Radiology, volume 142, pages 765–768 (1982)).

The most pertinent prior art related to the present invention are feedback controlled flux equalization x-ray radiography systems using a scanning fan beam of x-rays. Representative of the prior art are, as mentioned above, U.S. Pat. No. 4,433,430 (Fredzell) and an article by Plewes et al (Radiology, volume 142, pages 765–768 (1982)). The main advantages of these systems over the systems using the scanning pencil beam of x-rays are: (a) increased x-ray tube life with about 10 to 20 times reduction in heat loading through more efficient use of x-rays, (since heat loading is proportional to the ratio of the area of the imaged field to the area of the scanning aperture and the aperture used in scanning fan beam is usually 10 to 20 times larger than the aperture used in scanning pencil beam,) (b) less patient motion problem through shorter time required to complete the imaging process, (c) less scan artifacts because scanning pencil beam systems require accurate control of the spacing between overlapping scan lines and the size and profile of the x-ray spot, and (d) less cooling time of the x-ray tube associated with reduced heat loading means shorter wait between examinations and higher patient throughput.

The scanning fan beam systems also have many advantages over the systems using x-ray or optical masks. These advantages are: (a) no need of hassle in the making and subsequent registration or alignment of x-ray or optical masks, (b) much less patient misregistration problem resulting from much less time delay between the process of obtaining the patient attenuation information and final imaging process, and (c) much better rejection against scattered x-rays.

However, the main drawback of the fan beam systems taught by Fredzell and Plewes is that the flux equalization is only applied in the direction of the scan and not in the direction perpendicular to the scan. That is, the feedback signal is used to control the x-ray source intensity or duty cycle providing an uniform x-ray intensity across the entire fan beam. This one-dimensional feedback controlled flux equalization is unable to provide compensation to the entire image and is also prone to scan artifacts. Indeed, Plewes et al concluded in the same article that a scanning pencil beam system is the "only" way to overcome this drawback. The system taught by Fredzell has two fan beams. One fan beam is used as the monitoring beam to acquire patient attenuation information, and the second fan beam is used to image. However, since the same x-ray source is being used by both fan beams and the source intensity modulation would also affect the monitoring fan beam, it is not clear how the system's feedback control could function properly. It should also be obvious that Fredzell's systems could not support more than one imaging beam since each imaging beam would require a different modulation.

SUMMARY OF THE INVENTION

The above and other problems of x-ray fan beam type feedback controlled flux equalization imaging are overcome by the present invention of a scanning x-ray fan beam flux equalization system incorporating a dynamic feedback controlled flux modulation array means so that the x-ray intensity at a multiple number of points along the fan beam can be modulated in accordance with the need to compensate for the patient attenuation along the fan beam (in the direction perpendicular to the direction of the scan). The flux equalization system is interposed, for the most part, between the fan beam source and the imaging device and comprises a detector array located behind the patient for detecting the x-ray intensity transmitted through the patient at a multiple number of points along the fan beam and for generating an output signal representative of the detected x-ray intensity at such points, an x-ray flux modulator array located between the x-ray source and the patient for modulating the intensity of the x-ray fan beam at a multiple number of points along the fan beam in response to a control signal, and a feedback control circuit for processing the detector signal and then supplying the appropriate control signal to the flux modulator array to cause it to increase or decrease the x-ray flux at a multiple number of points along the fan beam until a substantially equal and predetermined flux level is detected by the detector.

In the preferred embodiment of this invention, the flux modulation is accomplished by modulating the local width of the fan beam with a movable shutter in the direction of the scan during the exposure at a multiple number of points across the fan beam. That is, the fan beam width is very broad over "thick" patient regions where the patient attenuation is very high, and the fan beam width is very narrow over "thin" patient regions where the patient attenuation is very low.

This method of flux modulation has two unique advantages. The first advantage is that the x-ray spectrum is essentially unchanged over the "thin" patient regions. This is not the case in Edholm et al and Mistretta et al. Their x-ray masks are made of x-ray absorbers which compensate for the patient attenuation in such a way that a thin absorber is used over the "thick" patient regions and a thick absorber is used over the "thin" patient regions. In this fashion, the soft component of the x-ray spectrum is preferentially removed (or the x-ray beam is hardened) from the "thin" patient regions where the soft component is needed the most to provide increased image contrast. The second advantage is that the effective exposure time over "thin" patient regions is very much shortened by the narrower fan beam width. Therefore, the patient motion problem in the "thin" patient regions, where the patient motion is most problemsome, is reduced. The local beam width modulation is not permitted in the scanning pencil beam devices of Craig et al and Plewes et al, because the pencil beam aperture size has to be held constant. Accordingly, this advantage allows the fan beam device to operate at an exposure time 10 to 20 times shorter than the pencil beam devices in "thin" patient regions.

The present invention retains all the advantages of fan beam feedback controlled flux equalization systems over the other feedback controlled flux equalization systems discussed in the sections above. It is a faster real time system as well as a more effective system with respect to the utilization of x-rays than the scanning pencil beam systems and is less susceptible to scan artifacts. Therefore, this invention is less susceptible to patient motion problems and also requires less heat loading to the x-ray tube. In addition, this invention has much better rejection against scattered x-rays than the x-ray mask systems of Edholm et al and Mistretta et al.

In another embodiment of this invention, several parallel scanning fan beams are used in unison so that the utilization of x-rays is further improved and the heat loading to the x-ray tube is further reduced. In a modification of this embodiment, the first scanning fan beam is used as a monitoring precursor beam and the trailing fan beams are flux equalized imaging fan beams. The monitoring fan beam is used only to collect the x-ray attenuation data at a low dose. The trailing imaging fan beams get the modulation signal from the feedback computer based on the data collected by the monitoring fan beam. Since the monitoring fan beam and the imaging fan beams are identical in construction, spatially well aligned with each other, and with short exposure time delays between the fan beams, the misregistration problems and patient motion problems are insignificant. This approach also uses fewer components and hence is lower in construction cost, because the monitoring beam does not need a flux modulator and all the trailing imaging beams do not need detector arrays.

It is therefore an object of the present invention to provide, in an x-ray radiography system, essentially real time feedback controlled flux equalization to the x-ray image recorder.

It is another object of the present invention to provide, in an x-ray radiography system, flux equalization without substantially altering the x-ray spectrum.

It is another object of the present invention to provide, in an x-ray radiography system, flux equalization with shorter exposure time to "thinner" regions of the patient.

It is another object of the present invention to provide, in an x-ray radiography system, flux equalization with increased rejection to scattered x-rays from the patient.

It is yet another object of the present invention to provide, in an x-ray radiography system, flux equalization with a minimum increase of heat loading to the x-ray tube.

It is yet a further object of the present invention to provide, in an x-ray radiography system, flux equalization with reduced patient motion problems, scan artifacts, and patient inconvenience.

These features and advantages of the present invention will become more apparent upon a perusal of the following specification taken in conjunction with the accompanying drawings wherein similar characters of reference refer to similar structures in each of the separate views.

BRIEF DESCRIPTION OF THE DRAWINGS

FIG. 1 is a diagrammatic, perspective view illustrating a first embodiment according to the invention;

FIG. 2 is a diagrammatic, sectional view, taken generally along the lines 2—2 in FIG. 1;

FIG. 3 is a diagrammatic, sectional view, taken generally along the lines 3—3 in FIG. 1;

FIG. 4 is a diagrammatic, vertical, sectional view of a second embodiment of the invention;

FIG. 5 is a diagrammatic, vertical, sectional view of a third embodiment of the invention;

FIG. 6 is an enlarged vertical, sectional view, with portions broken away, of the flux modulator of a fifth embodiment of the invention;

FIG. 7 is an enlarged, perspective view, with portions broken away and in section, of a flux modulator according to a sixth embodiment of the invention; and FIG. 8 is an enlarged vertical, sectional view, with portions broken away, of a flux modulator according to a seventh embodiment of the invention.

BEST MODE FOR CARRYING OUT THE INVENTION

Referring now more particularly to FIGS. 1, 2 and 3, an x-ray source 10 generates a broad x-ray beam 5 which impinges upon a first collimator 12 having a horizontal slot shaped aperture 14 for converting the x-ray beam 5 into a broad fan beam 7 which impinges upon a patient 18. Behind the patient is a second collimator 20 having a corresponding horizontal slot shaped aperture 22 which is aligned with the aperture 14. The collimator 20 substantially blocks patient scattered x-rays 19 from reaching the imaging panel 24. Aligned with the aperture 22 is an array 26 of individual detectors 28 which can be either x-ray detectors or photo-optic detectors depending upon the particular application. Interposed between the detector array 26 and the collimator 20 is the x-ray imaging panel 24 which can be either x-ray filmscreen cassette or storage phosphor cassette or Xerox cassette or other panel shaped image recorder, in which case the detectors 28 are x-ray detectors or it could be an x-ray image intensifier device optically coupled to film or TV camera or other image pick-up devices in which case the detectors could be photo-optic detectors.

The collimators 12 and 20 as well as the detector array 26 are connected together mechanically as indicated by the dashed line 32 to a motor drive 34. It is also equally feasible to drive these three elements with separate encoded motors to move in synchronism. Since such scanning apparatus is well known by those skilled in the art, it will not be described in further detail.

The outputs of the detectors 28 of the array 26 are fed to a closed loop feedback circuit 30 whose output controls a flux modulator 16 positioned over the aperture 14 of the first collimator 12. The feedback control circuit 30, in response to the output signals from the detectors 28, automatically reduces the x-ray flux passing through the aperture 14, by means of the flux modulator 16, so as to maintain a substantially equal and constant x-ray flux level at the input of the detectors 28, along the x-ray beam. Furthermore, this flux control is a dynamic process which is continually changing as the collimators 12 and 20 and the detector array 26 scan the body of the patient 18.

It is to be understood that when the term "equal flux level" is referred to it is not meant that at each minute point the x-ray flux exiting the patient is equal. Were this condition true, no diagnostic information would be available to the physician. Rather what is meant is that the average flux for a series of hypothetical "windows", whose areas correspond to the area covered by each detector (or a group of detectors), is equal across the fan beam. Within each such hypothetical window the x-ray flux will vary, depending on the x-ray image information.

Referring now more particularly to FIG. 6, a portion of one form of a flux modulator is illustrated. As can be seen in FIG. 2, the flux modulator 16 is made up of a group of individual cells 17 which are arrayed across the x-ray beam 5 coming from the source 10. Each cell 17 preferably corresponds to a portion of the x-ray beam which will impinge on one or more corresponding detectors 28 of the array 26. In order for a particular cell 17 to control the amount of x-ray flux striking a corresponding detector 28, it is necessary to reduce the cross-sectional area of the x-ray beam 5 by reducing the local width of the fan beam as it scans over the patient.

Thus, as shown in FIG. 6, each cell comprises a shutter 36 which is movable across the input of the aperture 14 of the collimator 12 to restrict the cross-sectional area of the x-ray beam 5. The shutter 36 is made of an x-ray opaque material, such as lead or tungsten or other metal and is operated by a servo motor 38 which receives its control signal either in digital or analog form from the feedback control 30. It will be understood that each cell 17 is provided with its own independent shutter 36 and servo motor 38 which operates under the control of the feedback circuit 30 responding to an output signal of a corresponding detector 28.

As the x-ray flux reaching a particular detector 28 increases above the preset standard value, the output of the detector will increase in magnitude and this increase will be fed back through the circuit 30 to the servo motor 38 of the corresponding flux modulation cell 17 aligned with that particular detector 28. This increase in the detector output signal will be transformed into a corresponding repositioning of the shutter element 36 to narrow the aperture 14 at the particular location across the x-ray beam. This will decrease the amount of x-ray flux accordingly until the output of the corresponding detector 28 reaches a predetermined reference level representative of the desired flux level.

Alternatively, the servo motor 38 can drive the shutter 36 into and out of the path of the beam 5 to turn the beam on for a desired duration or number of times at a higher frequency than the scan frequency (which is the number of apertures to cover the image field divided by the total scan time). This will in effect control the duty cycle of the beam and thus control the net amount of flux received both by the patient and by the corresponding detector 28. In this case, the duration or duty cycle of the beam on time is under the control of the output of the corresponding detector in the same manner as described above until the desired flux level is detected. That is, an increase in the output of the detector will cause the duration or duty cycle of the beam on time of the shutter 17 to increase until the output of the corresponding detector 28 is equal to the predetermined reference level.

Referring now more particularly to FIG. 7, a cell of a different type of modulation unit is depicted. In this system instead of a shutter blade 36 which is interposed into the path of the x-ray beam 5, a plurality of fingers 40 for each shutter blade replaced are individually inserted across the aperture 14. These fingers protrude from a electromechanical device 42, similar to a dot matrix printhead as used in a computer printer. Each finger is individually addressable in digital or analog fashion by the feedback control 30 in response to the output signal of a corresponding detector 28, in the manner described above in reference to FIG. 6.

Depending on the particular mechanism 42 utilized, the position of the fingers 40 can be discretely controlled or, in other embodiments, the fingers can be either inserted or removed from the path of the beam. In the first version, the extent of the total number of fingers into the beam determine the effective width of the aperture 14 at that flux modulation cell and thus the flux level. In the second modification, the number of fingers interposed into the beam versus the number of open spaces determines the flux level. In still a third modification, the duration at which the fingers are extended into and removed from the beam is controlled by the feedback control 30. Again, the duty cycle of the fingers within the beam determines the flux level in the manner described above in reference to the single shutter of FIG. 6.

The fingers 40 are made of an x-ray opaque material. Thus any portion of the x-ray beam which impinges upon the fingers will be effectively stopped and any portion of the x-ray beam which does not impinge upon the fingers will pass through to strike the patient and the detector array 26. The significant feature of all of the flux modulations schemes discussed above is that for the portion of the x-ray beam which passes through the aperture there has been no change in the x-ray spectrum. Thus low energy x-rays, which are generally needed to enhance the detection of low density tissues in the more transparent regions of the patient, such as the lung region, are not reduced or removed, thereby contributing to the diagnostic efficacy of this device.

Referring now to FIG. 4, another embodiment of the present invention is illustrated. In this embodiment, a plurality of x-ray fan beams 7a, 7b, 7c are used in unison to improve the utilization of x-rays and to decrease the heat loading on the x-ray. Each of the fan beams in this embodiment is constructed and operates substantially the same as the single fan beam described above and illustrated in FIGS. 1, 2, and 3. As illustrated in FIG. 4, each fan beam 7a, 7b, 7c has its own corresponding slots 14a, 14b, 14c and 22a, 22b, 22c, respectively in collimators 12 and 20, flux modulator arrays 17a, 17b, 17c, detector arrays 26a, 26b, 26c and feedback control circuits 30a, 30b, 30c, respectively.

In the case of FIG. 4, where three x-ray fan beams are depicted, the scan of the image can be accomplished in two different ways. One way is to scan the entire image field once with all three fan beams and with the x-ray tube operating at one-third of the rating required by the single fan beam system. Another way is use each fan beam to scan only one-third of the image field by spacing the fan beams at one-third of the image field width apart. In this way, the total scan time is reduced by a factor of three as compared to the total scan time of the single fan beam system. Both scan methods are capable of reducing the x-ray tube heat loading by approximately a factor of three, which equals the number of fan beams used.

Referring now more particularly to FIG. 5, another embodiment of the invention is illustrated. In this embodiment a plurality of fan beams are used again in unison to improve the utilization of x-rays, but the first fan beam (or the leading fan beam in the direction of scan) has been modified to be used as a monitoring precursor beam for the sole purpose of collecting the x-ray attenuation information at a low dose. As shown in FIG. 5, a plurality of imaging fan beams 7a, 7b, which are defined by the corresponding horizontal slot apertures 14a, 14b in the collimator 12, are modulated independently by flux modulator arrays 17a and 17b. These imaging fan beams are further collimated through the horizontal slot apertures 22a and 22b in the collimator 20 before impinging on the imaging panel 24.

Additionally, a low intensity x-ray monitoring fan beam 44, which is defined by a narrower horizontal slot aperture 14c in the collimator 12, is used with a detector array 26 to measure the x-ray attenuation of the patient. The detector array 26 is positioned immediately behind the horizontal slot aperture 22c in the collimator 20 and in front of the imaging panel 24. In all other respects the device depicted in FIG. 5 is constructed and operates substantially the same as that depicted in FIG. 4 with the following exceptions.

The collimators 12 and 20 are operated synchronously to scan the monitoring beam 44 over the entire length of the patient 18. However, the x-ray imaging beams are not only modulated in intensity by the modulation arrays 17a and 17b they are also turned on to only scan the upper and lower halves of the patient 18, respectively. Thus, in operation, the collimators 12 and 20 are positioned so that the monitoring beam 44 starts at the top of the head of the patient 18 (or it could also scan from the bottom to the top or from side to side as the case may be). The flux level information revealed by detecting this monitoring beam is collected by the detector array 26 and is stored in the feedback control computer 30 relative to the scan position of the aperture 22c.

As the collimators 12 and 20 reach the point where a line drawn between the apertures 14a and 22a would just intersect the top-most portion of the patient 18 (or whatever other portion of the patient 18 constitute the beginning of the imaging scan), the flux modulator arrays 17a and 17b are both opened to allow the x-ray image beams 7a and 7b to scan the patient 18. However, the flux modulator arrays 17a and 17b are operated under the control of the feedback computer 30 so that the flux modulation cells across the beams 7a and 7b are controlled to pass only the correct amount of x-ray flux and equal flux density is obtained at the screen 24. The computer 30 scans its memory bank for the stored output signals from the detector array 26 corresponding to the position of the x-ray beams 7a and 7b as they scan the patient. These signals are then used to control the flux modulators 17a and 17b as the image beams 7a and 7b scan over the same points on the patient's body that were previously scanned by the monitoring beam 44.

The scanning by the collimators 12 and 20 stops when the x-ray image beam 7b has reached the bottom of the patient 18. The spacing between the apertures 14a, 14b and 14c and between the apertures 22a, 22b and 22c is chosen so that there will be no overlapping of the scanning beams 7a and 7b in scanning the patient 18. Obviously, in other embodiments, more than two image scanning beams could be utilized in the same manner as described above in reference to the beams 7a and 7b.

This approach uses fewer components and is lower in construction costs than the embodiment described in reference to FIG. 4, because the monitoring beam does not need a flux modulator and all the trailing imaging beams do not need detector arrays. The fact that the monitoring fan beam does not have to perform imaging duties allows the detector array 26 to be conveniently placed in front of the imaging panel 24. This improvement in the placement of the detector array provides more freedom in the designs of the imaging panel as well as additional savings in the construction costs. Since the monitoring fan beam and the imaging fan beams are identical in construction, spacially well aligned with each other, and with short exposure time delays between the monitoring and image fan beams, the misregistration problems and patient motion problems are insignificant.

Referring now more particularly to FIG. 8, still a further alternative flux modulation cell is illustrated. In this modification the shutter 80, corresponding to the shutter 36 depicted in FIG. 6, is also controlled by a servo motor 38 which receives its control signals from the feedback circuit 30. Shutter 80 is wedge-shaped and is made of a material which attenuates x-rays passing through it. Thus the position of the wedge-shaped shutter 80 with respect to the aperture 14 controls the flux density of the x-ray beam 5 passing through it. As the portion of the wedge which intercepts the beam 5 is thicker, at one side of the wedge, more of the x-ray beam will be attenuated than if only the thin portion of the wedge is intercepted by the beam 5. This embodiment has the disadvantage that low energy x-rays are disproportionately attenuated in the "thin" regions of the patient.

More detailed considerations of the fan beam geometry and the flux modulator mentioned in the above embodiments will now be given. In order to obtain a reasonable x-ray utilization efficiency as well as good rejection against scattered x-rays, the size of the fan beam at the imaging plane (the plane of imaging panel 24) should be approximately between 10 mm to 40 mm in width (W) and 432 mm in length (G) for standard chest x-ray examinations. The width of the fan beam is proportional to the x-ray utilization efficiency and is inversely proportional to the x-ray tube heat loading required to perform the imaging scan, whereas the width of the fan beam is inversely proportional to the ability to reject scattered x-rays.

The flux modulator should be placed close to the x-ray source so that the fan beam width at the modulator (or the distance which the shutter blades have to cover during the modulation process) is small. However, if the modulator is placed too close to the x-ray source, the x-ray penumbra due to the finite size of the x-ray source (focal spot) becomes too large at the imaging plane and the equalization process becomes too gross (spatial frequency becomes too low) to be useful. For the above reasons, the ratio of the distance (D) between the flux modulator and the imaging panel to the distance (d) between the flux modulator and the x-ray source spot (focal spot) should be in the range of 5 to 25. That is, $$\frac{D}{d} = 5 \text{ to } 25.$$

For a practical x-ray focal spot (f) of 1.0 mm, the corresponding range of x-ray penumbra size (P) at the imaging plane for this range of placement of the flux modulator is 5 to 25 mm. That is, $$P = f\left(\frac{D}{d}\right).$$

For a fan beam with a width (W) of 22 mm, the range of the fan beam width at the flux modulator (w) is 3.67 to 0.85 mm, which is the distance to be covered by the shutter blades. That is, $$w = W/\left(1 + \frac{D}{d}\right).$$

In order to minimize sources of scan artifacts, the width (s) of the shutter blades should be sufficiently small so that its x-ray shadow on the imaging plane is within a factor of two from the size of the x-ray penumbra due to the focal spot size. That is, $$s \simeq f\left(\frac{(D/d)}{(D/d + 1)}\right).$$

Since the length (g) of the fan beam at the flux modulator is $$g = G/\left(1 + \frac{D}{d}\right),$$

then the number (N) of shutter blades in a flux modulator is simply g/s or $$N \simeq W/\left(f\frac{D}{d}\right)$$

For W=432 mm, f=1.0 mm, and D/d=10 to 20, then the number of shutter blades in a flux modulator is in the range of 40 to 20. At about D/d=20, the fan beam width at the flux modulator and the shutter blade width are both about 1.0 mm in size and the shutter blade thus has a square looking cross-section with respect to the x-ray beam. At D/d smaller that 20, the fan beam width becomes larger than the shutter blade width.

The shutter blade 36 can have a square or rectangular cross-section perpendicular to the x-ray fan beam, but the cross-section in the plane of the fan beam can be trapezoidal in order to have a better fit to the shape of the divergent fan beam.

The x-ray absorbing material used in the flux modulator shutter blade 36 as well as the wedge-shaped shutter 80 can be selected from a large number of material groups. For example, the material can be made from a metal or an alloy or a compound containing one or more the following elements: Pb, Bi, Ta, W, Mo, Cd, Fe, Ni, Cu, Co, Ba, Ce and rare-earth elements.

Each detector element 28 of the scanning detector 26 array can be an x-ray detector diode or it can be made, for example, of a scintillator, such as a rare-earth intensifying screen or a CsI screen or a BGO crystal, or a CdWO$_4$ crystal, coupled to a silicon diode light detector or a photomultiplier tube. The detector array can also be made of an array of gas ionization cells or a scintillator screen optically coupled, in contact or through a lens or a bundle of fiber optical light pipes, to an array of self scanned silicon diodes or a TV camera. An image intensifier can also be used as a part of the detector system to provide amplified signals.

The detector arrays 26 described in above embodiments are coupled to the fan beams and are moved in step with the fan beams. However, it is equally feasible in certain geometries, such as in the case of planar imaging panels like film-screen cassettes, these detector arrays are replaced by a stationary bank of strip shaped detector elements oriented perpendicular to the plane of fan beam. That is, each detector element 28 is made of a long strip detector with a length equal to the total width of the image field and is aligned with its corresponding flux modulator element 17 during the entire scan. These detector strips are very similar in shape and operation to those long detectors disclosed by Edholm et al (see U.S. Pat. No. 3,755,672, column 10, line 51 and FIG. 9).

The image recorder 24, for which the flux equalized information is provided, can be a simple x-ray film or a x-ray film-screen cassette. It can also be an automatic film changer or an image intensifier-film or image intensifier-TV system. It can also be a special imaging cassette, which is capable of storing a latent x-ray image for retrieval at a later time.

As explained above, in all of the embodiments, the feedback control circuit 30 derives a signal for the flux modulator based on the detected x-ray transmittance signal through the patient. The product of the x-ray transmittance of the flux modulator and the x-ray transmittance of the patient at any point of the image field must be held to a constant. That is, the transmittance of any one of the elements of the modulator 17 is varied in inverse proportion to the transmittance of the patient at the corresponding point so that the resultant signal received by the corresponding element of the detector 28 is essentially the same as the signal from all other detector elements.

More detail considerations of the systems operation of the present invention will now be given. A conventional radiography system for chest x-rays consists of typically a medium speed film-screen cassette, a 10:1 grid, a photo-timer, and a three-phase 12-pulse x-ray generator operating at 125 Kvp and 400 mA with a source-detector distance of 72 inches. For average patients, the typical exposure time is about 10 milliseconds for PA views and about 30 milliseconds for lateral views.

With a system incorporating only a single fan beam, the present invention will be able to provide feedback controlled flux equalized film with similar local exposure times and better rejection against scattered x-rays. The parameters of the system will be as follows. The size of the fan beam at the imaging plane will be 25 mm in width and 432 mm in length. The D/d will be about 15 to 20. The total scan time will be about one second The system will be operated with a medium speed film-screen cassette, a source-detector distance of 72 inches and without a grid. The generator will be operated at 125 Kvp and 150 mA for PA views and 450 mA for lateral views. With multiple fan beams, the system will have more flexibility and less heat loading.

Further improvement in diagnostic value can be obtained from the flux equalized films from the system of the present invention by employing x-ray films, with a gamma larger than 3, with higher contrast enhancement factors. Higher contrast films cannot be used with the conventional radiography systems where already large regions are either overexposed or underexposed It is obvious that the scanning of this system can carried out in any orientation or direction. However, for ease of construction, the direction of scan should be parallel to the spine of the patient 18. However, for better rejection against scattered x-rays, the scan direction should be perpendicular to the spine of the patient. It is also obvious that the present flux equalization invention can be applied to most of the medical radiography examinations as well as to industrial radiography examinations.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

What is claimed is:

1. A system for imaging an object with penetrating radiation comprising:
    a source which generates a monitoring beam and an imaging beam of penetrating radiation which scan an object one after the other in a scanning direction;
    a receptor which receives said monitoring beam and said imaging beam after said beams have passed through said object, wherein said receptor in response to said imaging beam forms an image of said object and in response to said monitoring beam generates an exposure control signal which varies as a function of a local response of the object to the monitoring beam both in the scanning direction and in a second direction which is transverse to the scanning direction; and
    a modulator which in response to said exposure control signal modulates said imaging beam, differently from any modulating of said monitoring beam, before the imaging beam impinges on said object, the modulation of said imaging beam varying both in the scanning direction and in said second direction to control the local level of exposure delivered to said receptor by said imaging beam.

2. A system as in claim 1 including means for scanning said monitoring beam and said imaging beam concurrently over at least a portion of said object.

3. A system as in claim 1 in which said receptor comprises a detector which receives said monitoring beam and generates said exposure control signal and an image which receives said imaging beam and forms said image of said object.

4. A system as in claim 1 in which said monitoring beam delivers to said object a low dose of said penetrating radiation as compared with said imaging beam.

5. A system as in claim 1 in which said modulator comprises a plurality of shutters arrayed along said second direction which modulate respective portions of said imaging beam by locally changing the cross-section of said portions while substantially maintaining the spectrum of the imaging beam impinging on said object.

6. A system as in claim 1 in which each of at least a number of said shutters comprises a bundle of fingers of x-ray blocking material, wherein the fingers of a bundle are individually movable relative to other fingers in the same bundle in response to said exposure control signal to modulate respective sub-portions of said imaging beam.

7. A system as in claim 1 in which each of at least a number of said shutters comprises a bundle of fingers of x-ray blocking material, wherein the fingers within a bundle modulate the respective sector of the imaging beam by varying at least one of: (i) the extent to which the entire bundle intercepts said sector at any one time; (ii) the number of fingers which intercept said sector relative to the number of fingers which do not at any one time; and (iii) the durations of periods during which at least some of the fingers within a bundle intercepts said sector relative to the durations of periods during which they do not.

8. A system for imaging an object with penetrating radiation comprising:
a source which generates an imaging beam of penetrating radiation scanning an object in a scanning direction;
a receptor which receives said imaging beam after said beam has passed through said object and in response to the received imaging beam forms an image of said object and generates an exposure control signal related to the local response of said object to said imaging beam, said control signal varying with said local response both in the scanning direction and in a second direction which is transverse to the scanning direction; and
a modulator which in response to said exposure control signal modulates said imaging beam before the imaging beam impinges on said object, the modulation varying both in the scanning direction and in said second direction to control the local level of exposure delivered to said receptor by said imaging beam;
wherein said modulator comprises a plurality of shutters arrayed along said second direction which modulate respective portions of said imaging beam by locally changing the cross-sections of said portions while substantially maintaining the spectrum of the imaging beam impinging on the object.

9. A system as in claim 8 in which said receptor comprises: (i) a detector which receives radiation related to said imaging beam after passage thereof through said object and in response thereto generates said exposure control signal; and (ii) an imager which receives said imaging beam and in response thereto forms said image of said object.

10. A system as in claim 9 including means for scanning said detector relative to said object concurrently with said imaging beam.

11. A system as in claim 8 in which each of at least a number of said shutters comprises a bundle of fingers of x-ray blocking material which modulate respective sub-portions of said imaging beam.

12. A system as in claim 8 in which each of at least a number of said shutters comprises a bundle of fingers of x-ray blocking material, wherein the fingers within a bundle modulate the respective sector of the imaging beam by varying at least one of: (i) the extent to which the entire bundle intercepts said sector at any one time; (ii) the number of fingers which intercept said sector relative to the number of fingers which do not at any one time; and (iii) the durations of periods during which at least some of the fingers within a bundle intercepts said sector relative to the durations of periods during which they do not.

13. A system as in claim 8 in which said imaging beam is fan-shaped when impinging on said modulator, and said shutters selectively intercept respective sectors of said fan-shaped beam.

14. A system as in claim 8 in which the thickness of a shutter is substantially constant along the direction of propagation of the respective portion of said imaging beam.

15. A system as in claim 8 including means for scanning said shutters relative to said object concurrently with said imaging beam.

16. A system as in claim 8 in which said source comprises an x-ray tube and said receptor comprises an x-ray film.

17. A system for imaging an object with penetrating radiation comprising:
a source which generates an imaging beam of penetrating radiation scanning an object in a scanning direction;
a receptor which receives said imaging beam after said beam has passed through said object and in response to the received imaging beam forms an image of said object and generates an exposure control signal related to the local response of said object to said imaging beam, said control signal varying with said local response both in the scanning direction and in a second direction which is transverse to the scanning direction; and
a modulator which in response to said exposure control signal modulates said imaging beam before the imaging beam impinges on said object, the modulation varying both in the scanning direction and in said second direction to control the local level of exposure delivered to said receptor by said imaging beam by reducing the average local exposure time of said object by said portions of said imaging beam, absent velocity modulation, as compared to the average local exposure time if said portions were not modulated, through controlling at least one of the local cross-section and the local presence of radiation exiting the modulator.

18. A system as in claim 17 in which said modulation comprises beam width modulation in which the cross-section of each of at least a number of said portions of said imaging beam is selectively changed during said scanning of said object by said imaging beam.

19. A system as in claim 17 in which said modulation comprises pulse width modulation in which at least a part of each of at least a number of portions of said imaging beam is kept from reaching said object over selected proportions of time intervals which are fractions of the time which the imaging beam takes to scan the object.

20. A system as in claim 17 in which said modulation comprises pulse width modulation in which each of at least a number of portions of said imaging beam is kept from reaching said object over selected proportions of time intervals which are fractions of the time which the imaging beam takes to scan the object.

21. A method of imaging an object with penetrating radiation comprising:

scanning an object in a selected scanning direction first with a monitoring beam and then with an imaging beam of penetrating radiation;

receiving said monitoring beam and said imaging beam after said beams have passed through said object, and: (i) in response to the received monitoring beam generating an exposure control signal which varies as a function of a local response of the object to the monitoring beam both in the scanning direction and in a second direction which is transverse to the scanning direction, and (ii) in response to the received imaging beam forming an image of said object; and modulating said imaging beam, differently from any modulating of said monitoring beam, as a function of said exposure control signal before the imaging beam impinges on said object, the modulation of said imaging beam varying both in the scanning direction and in said second direction, to control the local level of exposure delivered to said receptor by said imaging beam.

22. A method as in claim 21 in which said monitoring beam delivers substantially constant exposure to said object while scanning.

23. A method as in claim 21 in which said monitoring beam and said imaging beam concurrently scan said object for at least a part of said scanning.

24. A method as in claim 21 in which said receiving step comprises using a detector which receives said monitoring beam and generates said exposure control signal and using an imager which receives said imaging beam and forms said image of said object.

25. A method as in claim 21 in which said monitoring beam irradiates said object at a low dose of said penetrating radiation as compared with said imaging beam.

26. A method as in claim 21 in which said modulation comprises beam width modulation of respective portions of said imaging beam.

27. A method as in claim 26 in which said beam width modulation comprises using a plurality of shutters arrayed along said second direction which modulate respective portions of said imaging beam by locally changing the cross-section of said portions without substantially altering the spectrum of the imaging beam impinging on the object.

28. A method as in claim 21 in which said modulation comprises pulse width modulation of respective portions of said imaging beam.

29. A method of imaging an object with penetrating radiation comprising:

scanning an object in a scanning direction with an imaging beam of penetrating radiation;

receiving said imaging beam after said beam has passed through said object and in response to the received beam forming an image of said object and generating an exposure control signal related to the local response of said object to said imaging beam, said exposure control signal varying with said local response both in the scanning direction and in a second direction which is transverse to the scanning direction; and modulating said imaging beam, by locally changing the cross-sections of said portions without substantially altering the spectrum of the imaging beam, as a function of said exposure control signal before the imaging beam impinges on said object, the modulation varying both in the scanning direction and in said second direction, to control the local level of exposure delivered to said receptor by said imaging beam.

30. A method as in claim 29 in which said receiving of the imaging beam comprises using a detector which receives said imaging beam and in response thereto generates said exposure control signal and using an imager which receives said imaging beam and in response thereto generates said image of said object.

31. A method as in claim 29 in which said detector scans said object concurrently with said imaging beam.

32. A method as in claim 29 in which said imaging beam is fan-shaped.

33. A method of imaging an object with penetrating radiation comprising:

generating an imaging beam of penetrating radiation scanning an object in a scanning direction, where the portions of the beam scan at the same speed;

receiving said imaging beam after said beam has passed through said object and in response to the received imaging beam forming an image of said object and generating an exposure control signal related to the local response of said object to said imaging beam, said control signal varying with said local response both in the scanning direction and in a second direction with is transverse to the scanning direction; and modulating said imaging beam, as a function of said exposure control signal, before the imaging beam impinges on said object, the modulation varying both in the scanning direction and in said second direction to control the local level of exposure delivered to said receptor by said imaging beam by reducing the average local exposure time of said object by portions of said imaging beam, absent velocity modulation, as compared to the average local exposure time if said portions were not modulated.

34. A method as in claim 33 in which said modulation comprises beam width modulation in which the cross-section of each of at least a number of said portions of said imaging beam is selectively changed during said scanning of said object by said imaging beam.

35. A method as in claim 33 in which said modulation comprises pulse width modulation in which at least a part of each of at least a number of portions of said imaging beam is kept from reaching said object over selected proportions of time intervals which are fractions of the time which the imaging beam takes to scan the object.

36. A method as in claim 33 in which said modulation comprises pulse width modulation in which each of at least a number of portions of said imaging beam is kept from reaching said object over selected proportions of time intervals which are fractions of the time which the imaging beam takes to scan the object.

37. A method as in claim 33 in which said step of receiving the imaging beams and forming an image of said object comprises forming said image on an x-ray film having a gamma greater than 3.

38. A method as in claim 29 in which said step of receiving the imaging beams and forming an image of said object comprises forming said image on an x-ray film having a gamma greater than 3.

39. A method as in claim 21 in which said step of receiving the imaging beams and forming an image of said object comprises forming said image on an x-ray film having a gamma greater than 3.

40. A system as in claim 17 in which said receptor forming an image of said object comprises an x-ray film having a gamma greater than 3.

41. A system as in claim 17 in which said modulator comprises modulator shutters arrayed in a direction transverse to the scanning direction and selectively intercepting respective portions of the imaging beam during said scanning, wherein the number of said shutters is at least 20.

42. A system as in claim 41 in which the number of said shutters is in the range of 20 to 40.

43. A system as in claim 8 in which the number of said shutters is at least 20.

44. A system as in claim 43 in which the number of said shutters is in the range of 20 to 40.

45. A system as in claim 8 in which said receptor which forms said image of said object comprises an x-ray film having a gamma greater than 3.

46. A system as in claim 1 in which said modulator comprises modulator shutter arrayed in said second direction and selectively intercepting respective portions of the imaging beam during said scanning, wherein the number of said shutters is at least 20.

47. A system as in claim 46 in which the number of said shutters is in the range of 20 to 40.

48. A system as in claim 1 in which said receptor which forms said image of said object comprises an x-ray film having a gamma greater than 3.

49. An x-ray machine comprising:
an x-ray tube which generates an x-ray beam;
a collimator which forms said x-ray beam into a fan-shaped beam;
a modulator which is between said collimator and said object and modulates the fan-shaped beam to form a modulated beam which impinges on an object;
said collimator scanning relative to an object to scan the object with said modulated beam in a scanning direction;
a receptor which receives said modulated beam after the modulated beam has passed through said object and in response forms an x-ray image of said object;
a feedback system which also receives said modulated beam after the modulated beam has passed through said object and in response generates feedback measurements related to the local response of said object to the modulated beam;
said feedback measurements varying with the local response both in said scanning direction and in a direction transverse to the scanning direction;
said modulator comprising a row of about 20 to about 40 elements which are arrayed along said transverse direction at positions corresponding to respective sectors within the fan-shaped beam and: (i) each element is movable relative to said collimator to block a portion of the cross-section of the corresponding sector of the fan beam; (ii) the blocked portion varies as a function of said feedback measurements during the scan of the object with said modulated beam; and (iii) the element substantially totally prevents the x-rays of the blocked portion of the sector from reaching the object.

50. An x-ray machine as in claim 49 in which the feedback system comprises a respective detector for each of the modulator elements, each detector generating a feedback measurement used in controlling the movement of the respective element relative to the collimator.

51. An x-ray machine as in claim 50 including means for scanning the modulator relative to the object together with the collimator.

52. An x-ray machine as in claim 51 in which said feedback measurements are related to the attenuation which respective x-ray sectors have suffered in passing through the object over respective periods during said scanning of the object with said modulated beam.

* * * * *

UNITED STATES PATENT AND TRADEMARK OFFICE
CERTIFICATE OF CORRECTION

PATENT NO. : 4,953,189

DATED : August 28, 1990

INVENTOR(S) : Shih-Ping Wang

It is certified that error appears in the above-identified patent and that said Letters Patent is hereby corrected as shown below:

Column 13, line 3 (Claim 6, line 1), change "1" to --5--.

Column 13, line 10 (claim 7, line 1), change "1" to --5--.

Column 17, line 39 (claim 49, line 6), change "said" to --an--;
line 40 (claim 49, line 7), change "an" to --said--.

Signed and Sealed this

Sixth Day of October, 1992

Attest:

DOUGLAS B. COMER

*Attesting Officer*  *Acting Commissioner of Patents and Trademarks*